US006506417B1

(12) United States Patent
Siddle

(10) Patent No.: US 6,506,417 B1
(45) Date of Patent: Jan. 14, 2003

(54) COMPOSITION AND PROCESS FOR REDUCING BACTERIAL CITRUS CANKER ORGANISMS

(75) Inventor: John M. Siddle, Lakeland, FL (US)

(73) Assignee: FMC Technologies, Inc., Chicago, IL (US)

( * ) Notice: Subject to any disclaimer, the term of this patent is extended or adjusted under 35 U.S.C. 154(b) by 34 days.

(21) Appl. No.: 09/894,570

(22) Filed: Jun. 28, 2001

(51) Int. Cl.$^7$ .................. A01N 37/00; A01N 37/16; A01N 59/00; A61L 21/18; A23L 3/34

(52) U.S. Cl. .................. 424/616; 514/557; 514/558; 514/559; 514/560; 514/568; 514/572; 514/574; 514/714; 422/28; 422/29; 426/333; 426/335; 426/532

(58) Field of Search .................. 514/557–560, 514/568, 572, 574, 714; 424/616; 422/28, 29; 426/333, 335, 532

(56) References Cited

U.S. PATENT DOCUMENTS

| 5,674,538 A | 10/1997 | Lokkesmo et al. |
| 5,996,485 A | 12/1999 | Suter et al. |
| 6,165,483 A | * 12/2000 | Hei et al. .................. 424/405 |
| 6,302,968 B1 | * 10/2001 | Baum et al. .................. 134/30 |

FOREIGN PATENT DOCUMENTS

| EP | 242990 | * 10/1987 |
| EP | 0 945 405 A | 9/1999 |
| GB | 1 571 357 A | 7/1980 |
| WO | WO 92 19287 A | 11/1992 |
| WO | 94/06294 | * 3/1994 |
| WO | WO 94 23575 A | 10/1994 |
| WO | WO 98 37762 A | 9/1998 |

OTHER PUBLICATIONS

Approved Decontamination Products & Methods. Florida Dept. of Agriculture and Consumer Services, Aug. 2002 [Retrieved on Sep. 17, 2002].*
Retrieved from the Internet: URL: http://doacs.state.fl.US/Canker/Decontamination.Pdf. Aug. 2002.*
T.S. Schubert and J. W. Miller, *Bacterial Citrus Canker, Plant Pathology Circular No. 377*, Fla. Dept. Agric. & Consumer Services, Division of Plant Industry, May/Jun. 1996 (Revised Jul. 1998)(pp. 1–6; PL–96t–25).
Will Wardowski, *Citrus Canker Packinghouse Procedures, Packinghouse Newsletter No. 185*, University of Florida Cooperative Extension Service, Institute of Food and Agricultural Sciences, Mar. 19, 1999 (pp. 1–2), Gainesville, Florida.
*Rules Of The Department Of Agriculture And Consumer Services, Division of Plant Industry*, Chapter 5B–58, *Citrus Canker*, (pp. 1–6)(new Jan. 17, 1996; amended Jul. 17, 2000).
Tim Schubert, Wayne Dixon and Xiaoan Sun, *Citrus Canker, The threat to Florida agriculture, Summary of the Justification for Removing Canker–Exposed Trees within 1900 Feet of Infected Trees*, Florida Department of Agriculture and Consumer Services, (pp. 1–2) updated Jun. 7, 2000.
*Products Approved For Decontamination*, List revised Feb. 12, 2001.
Florida Department Of Agriculture & Consumer Services, *Citrus Canker in Florida (through Feb. 23, 2001)*, (pps. 2).
Baldry, M.G.C., *The bactericidal, fungicidal and sporicidal properties of hydrogen peroxide and peracetic acid*, Journal of Applied Bacteriology 54, Research and Development Department, Interox Chemicals Limited, Moorfield Road, Widnes, Cheshire W A8 OJU UK, 1982, (pp. 417–423).
Jim R. Wright, Susan S. Sumner, Cameron R. Hackney, Merle D. Pierson and Bruce W. Zoecklein, *Reduction of Escherichia coli 0157:H7 on Apples Using Wash and Chemical Sanitizer Treatments*, Dairy, Food and Environmental Sanitation, vol. 20, No. 2, Feb. 2000 (pp. 120–126, Des Moines, IA.
C. M. Park and L. R. Beuchat, *Evaluation of Sanitizers for Killing Escherichia coli 0157:H7, Salmonella, and Naturally Occurring Microorganisms on Cantaloupes, Honeydew Melons, and Asparagus*, Dairy, Food and Environmental Sanitation, vol. 19, No. 12, (pp. 842–847), Des Moines, IA (12/99).
Steven Pao and Craig L. Davis, *Enhancing Microbiological Safety of Fresh Orange Juice by Fruit Immersion in Hot Water and Chemical Sanitizer*, Journal of Food Protection, vol. 62 No. 7, 1999 (pp. 756–760).
Frank P. Greenspan and Donald G. MacKellar, *The Application of Peracetic Acid Germicidal Washes to Mold Control of Tomatoes*, Food Technology, Mar. 1951, Buffalo, New York (pp. 95–97).
D. Coates, *Sporicidal activity of sodium dichloroisocyanurate, peroxygen and glutaraldehyde disinfectants agaist Bacillus subtilis*, Journal of Hospital Infection, 996, 32, (pp. 283–294).
Anouar Alasri, Michele Valverde, Christine Roques and Georges Michel and Corinne Cabassud and Philippe Aptel, *Sporocidal properties of peracetic acid and hydrogen peroxide, alone and in combination, in comparison with chlorine and formaldehyde for ultrafiltraion membrane disinfection*, Can. J. Microbiol., vol. 39, 1993 Toulouse, France, (pp. 52–60).

(List continued on next page.)

*Primary Examiner*—John Pak
(74) *Attorney, Agent, or Firm*—Allen, Dyer, Doppelt, Milbrath & Gilchrist, P.A.

(57) ABSTRACT

A disinfectant composition is disclosed effective against a pathovar of *Xanthomonas axonopodis* pathogenic for citrus, comprising an aqueous solution of a carboxylic acid, hydrogen peroxide, and a percarboxylic acid product thereof. In a preferred composition the percarboxylic acid comprises peroxyacetic acid in an equilibrium aqueous solution with hydrogen peroxide, and acetic acid. The composition is used in a process to disinfect citrus fruit and equipment used therewith by contacting with a sufficient concentration of the composition for a sufficient time for reducing the organisms by at least 99.9%.

20 Claims, No Drawings

OTHER PUBLICATIONS

Nelio J. Andrade, Tracy A. Bridgeman and Edmund A. Zottola, *Bacteriocidal Activity of Sanitizers against Enterococcus faecium Attached to Stainless Steel as Determined by Plate Count and Impedance Methods*, Journal of Food Protection, vol. 61, No. 7, 1998 (pp. 833–838).

Bridget L. Farrell, Amy B. Ronner and Amy C. Lee Wong, *Attachment of Escherichia coli, 0157:H7 in Ground Beef to Meat Grinders and Survival after Sanitation with Chlorine and Peroxyacetic Acid*, Journal of Food Protection, vol. 61, No. 7, 1998 (pp. 817–822).

D. Lindsay and A. von Holly, *Different Responses of Planktonic and Attached Bacillus subtilis and Pseudomonas fluorescens to Sanitizer Treatment*, Journal of Food Protection, vol. 62, No. 4, 1999 (pp. 368–379).

Barbara Blakistone, Rolenda Chuyate, Donald Kautter, Jr., James Charbonneau and Karen Suit, *Efficacy of Oxonia Active Against Selected Spore Formers*, Journal of Food Protection, vol. 62, No. 3, 1999 (pp. 262–267).

Payman Fatemi and Joseph F. Frank, *Journal of Food Protection*, vol. 62, No. 7, 1999 (pp. 761–765).

M. Arturo–Schaan, F. Sauvager, C. Mamez, A.Gougeon and M. Cormier, *Use of Peracetic Acid as a Disinfectant in a Water–Treatment Plant: Effect on the Plasmid Contents of Escherichia coli strains*, Current Microbiology, vol. 32, 1996 (pp. 43–47).

A. Jolivet–Gougeon, A. S. Braux, F. Sauvager, M. Arturo––Schaan and M. Cormier, *Can. J. Microbiol.*, 42, 1996 (pp. 60–65), Canada.

Jose–Luis Sagripanti and Aylin Bonifacino, *Comparative Sporicidal Effects of Liquid Chemical Agents*, Applied and Environmental Microbiology, vol. 62, No. 2, Feb. 1996, (pp. 545–551).

R. J. W. Lambert, M. D. Johnston and E.–A. Simons, *A kinetic study of the effect of hydrogen peroxide and peracetic acid against Staphylococcus aureus and Pseudomonas aeruginosa using the Bioscreen disinfection method*, Journal of Applied Microbiology 87, 1999 (pp. 782–786).

G. Eldon Brown, *Use of Xanthomonas campestris pv. Vesicatoria to Evaluate Surface Disinfectants for Canker Quarantine Treatment of Citrus Fruit*, Plant Disease, vol. 71 No. 4, Apr. 1987, (pp. 319–323).

M. Mari, T. Cembali, E. Baraldi and L. Casalina, *Peracetic Acid and Chlorine Dioxide for Postharvest Control of Monilinia laxa in Stone Fruits, Plant Disease,* vol. 83 No. 8, Aug. 1999 (pp. 773–776).

*AOAC Official Methods Of Analysis,* Chapter 6, *Disinfectants,* (pp. 9–11) (1995).

Web page printout from U.S. Environmental Protection Agency web site, DIS/TSS–4 Jan. 30, 1979, *Efficacy Data Requirements, Sanitizing rinses (for previously cleaned food–contact surfaces*), Office of Pesticide Programs, (one page).

*American Society For Testing And Materials, Standard Test Method for Efficacy of Sanitizers Recommended for Inanimate Non–Food Contact Surfaces,* (reprinted from the Annual Book of ASTM Standards), (pp. 1–4) (1994).

* cited by examiner

COMPOSITION AND PROCESS FOR REDUCING BACTERIAL CITRUS CANKER ORGANISMS

FIELD OF THE INVENTION

The present invention relates to the field of citrus fruit and, more particularly, to a disinfectant composition and process of using the composition for reducing *Xanthomonas axonopodis* organisms on citrus fruit and on equipment used with citrus.

BACKGROUND OF THE INVENTION

*Xanthomonas axonopodis* pathovar (pv) *citri* is recognized as the agent of bacterial citrus canker, a highly virulent contagious disease of citrus trees which has great economic importance in all citrus growing regions of the world. Official nomenclature for this organism was changed in the 1980s from *X. campestris* pv. *citri* to *X. axonopodis* pv. *citri* so that some of the prior literature will refer to the agent of bacterial citrus canker by its old designation.

*X. axonopodis* pv. *citri* is highly virulent for citrus crops, and its propagation for research purposes is, therefore, restricted to certain laboratories in the U.S. Department of Agriculture and the Florida Department of Agriculture and Consumer Services. A closely related pathovar, *X. axonopodis* pv. *citrumelo*, is the causative agent of citrus spot, a much less virulent disease than citrus canker, and is accepted as a model citrus pathogen representative of the more virulent citrus canker strain for general laboratory studies. Accordingly, *X. axonopodis* pv. *citrumelo* is the model organism employed for studies related to the present invention. *X. axonopodis* pv. *citrumelo* produces citrus spot, but tends to affect primarily nursery seedlings, rather than mature trees. A third related species sometimes found in literature reports is *X. axonopodis* pv. *vesicatoria*, causative agent of tomato spot. This pathovar is not a pathogen of citrus fruit or citrus trees.

G. Eldon Brown and T. S. Schubert proposed the use of *Xanthomonas campestris* pv. *vesicatoria* as a test model organism for use in testing the effectiveness of disinfectants against the agent of bacterial citrus canker. As part of this evaluation, they tested the effectiveness of peroxyacetic acid against the model organism, and determined that peroxyacetic acid at a concentration of 200 $\mu$g/ml produced an acceptable level of eradication comparable to approved chlorine treatments. Use of *Xanthomonas campestris* pv. *vesicatoria* to Evaluate Surface Disinfectants for Canker Quarantine Treatment of Citrus Fruit, pp. 319–323, Plant Disease, April 1987. Brown and Schubert did not test peroxyacetic acid against *Xanthomonas axonopodis*, nor did they test for effectiveness at concentrations lower than 200 $\mu$g/ml. In addition, pathovars, or strains, of Xanthomonas are very specific in their host range, that is, they are not cross-infective from one plant species to another. Thus, the citrus pathogens will not infect tomatoes, and the tomato pathogens will not infect citrus. It should be noted, however, that *X. axonopodis* pv. *citrumelo* was unknown at the time Brown and Schubert conducted their study, therefore they employed the nearest strain possible to *X. axonopodis* pv. *citri*. Nevertheless, the results published by Brown and Schubert, generated using a tomato pathogen, may not be predictably extrapolated to a citrus pathogen.

The control of infection and spread of these microbial plants pathogens has been a troublesome problem for many years in the citrus industry. Certain citrus growing areas, through governmental regulatory agencies, require control of these organisms on citrus fruit surfaces and on citrus fruit processing equipment. Treatments presently approved for control of these microorganisms on citrus fruit and on processing equipment include quaternary ammonium compounds, which have a tendency to injure the fruit, producing blemishes and potentially rendering the citrus fruit unfit for human consumption.

In addition, quaternary ammonium compositions exhibit residual activity which remains on the fruit processing equipment after drying following application of the sanitizer. Such residual activity may also injure the fruit during processing, producing blemishes and possibly making the fruit unmarketable.

SUMMARY OF THE INVENTION

With the foregoing in mind, the present invention advantageously provides a disinfectant composition for substantially reducing bacterial citrus canker organisms on citrus fruit and citrus fruit processing equipment.

The composition comprises from approximately greater than 10 to less than 100 parts per million of peroxyacetic acid in an equilibrium aqueous solution with hydrogen peroxide, and acetic acid.

Additionally, the composition is used in a process substantially reducing bacterial citrus pathogen organisms on citrus fruit and citrus fruit processing equipment by contacting with a sufficient concentration of peroxyacetic acid and for a sufficient time for reducing the citrus pathogen organisms by at least 99.9%.

The composition and process of the present invention provide broad spectrum activity against bacterial citrus pathogens and other microbial contaminants. The composition is effective at temperatures from about 5° C. to about 40° C. (41° to 104° F.), and at a pH up to about 8.0. Further, the composition once applied will degrade into harmless compounds including acetic acid, oxygen, water and carbon dioxide. The generally acidic pH of the composition tends to help remove mineral deposits from fruit processing equipment. The composition also exhibits low corrosiveness and will not harm stainless steel citrus fruit processing equipment. Because the composition chemically degrades after application, the process requires no rinsing after disinfection, thus saving time and water.

DETAILED DESCRIPTION OF THE PREFERRED EMBODIMENT

The present invention will now be described more fully hereinafter. This invention may, however, be embodied in many different forms and should not be construed as limited to the described embodiments set forth herein. Rather, these embodiments are provided so that this disclosure will be thorough and complete, and will fully convey the scope of the invention to those skilled in the art.

The invention discloses a disinfectant composition effective against a pathovar of *Xanthomonas axonopodis* pathogenic for citrus. The composition comprises an aqueous solution of a carboxylic acid, hydrogen peroxide, and a percarboxylic acid product thereof. An embodiment of the composition comprises a percaboxylic acid in combination with hydrogen peroxide, and preferably in an equilibrium aqueous solution with hydrogen peroxide, and acetic acid. Such an embodiment of the composition of the invention may be expressed in the following exemplary formulas.

$$CH_3COOH + H_2O \rightleftarrows CH_3OOOH + H_2O$$
Acetic Acid (HOAc) + Hydrogen Peroxide ⇌ Peracetic Acid (PAA) + Water $$K_{eq} = \frac{[PAA][H_2O]}{[HOAc][H_2O_2]}$$

PKa PAA = 8.2    PKa HOAc = 4.7

The disinfectant composition optionally may include up to approximately 1% by weight of sulfuric acid, to provide enhanced antimicrobial action. Additionally, the composition comprises at least approximately 10 parts per million of the percarboxylic acid, and more preferably at least approximately 30 parts per million of the percarboxylic acid. For use, an effective concentration of the composition includes less than approximately 85 parts per million of the percarboxylic acid.

The disinfectant composition should include sufficient percarboxylic acid to reduce the pathovar by at least 99.9%, and preferably to accomplish the reduction within less than approximately five minutes of contact time.

Another preferred embodiment of the disinfectant composition comprises less than 200 parts per million of peroxyacetic acid in an equilibrium aqueous solution with hydrogen peroxide, and acetic acid. As described above, this embodiment of the disinfectant composition may optionally include up to approximately 1% by weight of sulfuric acid. This composition also comprises at least approximately 30 parts per million of peroxyacetic acid. The peroxyacetic acid embodiment of the disinfectant composition preferably contains sufficient peroxyacetic acid to reduce said pathovar by at least 99.9%, and to do so within less than approximately one minute of contact time. A concentrate suitable for use dilution to prepare this embodiment of the disinfectant composition of the present invention is available from FMC Corporation, Active Oxidants Division, 1735 Market Street, Philadelphia, Pa. 19103, and is marketed under the tradename VigorOX™. The composition disclosed herein, however, contains a much lower concentration of peroxyacetic acid than previously recommended as a sanitizer in food processing.

The present invention also includes a process of disinfecting citrus fruit, comprising contacting the fruit with a composition effective against a pathovar of *Xanthomonas axonopodis* pathogenic for citrus, wherein the composition comprises an aqueous solution of a carboxylic acid, hydrogen peroxide, and a percarboxylic acid product thereof. In this process the step of contacting comprises less than 200 parts per million of the percarboxylic acid, for a time sufficient for reducing the pathovar by at least 99.9%, preferably within approximately one minute. In this process, contacting.optionally comprises up to approximately 1% sulfuric acid. The process may further include drying after contacting.

Yet another embodiment of the process of disinfecting fruits comprises contacting the fruit with a composition effective against a pathovar of *Xanthomonas axonopodis* pathogenic for citrus wherein the composition comprises less than 200 parts per million of peroxyacetic acid in an equilibrium aqueous solution with hydrogen peroxide, and acetic acid. As before, contacting comprises at least a 99.9% reduction in the target pathovar, preferably occurring within approximately one minute. In this embodiment of the process contacting may also comprise up to approximately 1% sulfuric acid, and may include drying after contacting.

The invention also discloses a process of disinfecting equipment used with citrus fruit, including all equipment involved in cultivating, harvesting, and processing citrus, whether manual or mechanical equipment, and including vehicles. An exemplary, but not limiting list of such equipment includes hand tools, implements, and machines for cultivating, harvesting, and processing citrus, containers for collecting and transporting harvested fruit, and transport vehicles. The process of disinfecting equipment used with citrus fruit comprises contacting the equipment with a composition effective against a pathovar of *Xanthomonas axonopodis* pathogenic for citrus, wherein the composition comprises an aqueous solution of a carboxylic acid, hydrogen peroxide, and a percarboxylic acid product thereof. As for fruit, disinfecting equipment involves contacting with less than 200 parts per million of the percarboxylic acid, and substantially reducing comprises at least a 99.9% reduction, preferably within approximately five minutes. Contacting may further comprise up to approximately 1% sulfuric acid, and drying after contacting.

The process of disinfecting equipment preferably includes contacting with a composition having less than 200 parts per million of peroxyacetic acid in an equilibrium aqueous solution with hydrogen peroxide, and acetic acid. In this embodiment of the process substantially reducing also comprises at least a 99.9% reduction, and preferably within approximately five minutes. As noted before, contacting optionally comprises up to approximately 1% sulfuric acid in the composition, and includes drying after contacting.

The following examples are provided to show the effectiveness of the claimed composition against a pathovar of *Xanthomonas axonopodis* pathogenic for citrus.

EXAMPLE 1

Tables 1 through 10 listed below show the effectiveness of the present composition against bacterial citrus spot organisms. It should be noted that concentrations below 100 parts per million demonstrate sufficient activity against bacterial citrus spot, as described herein.

Testing was performed according to AOAC (Association of Official Analytical Chemists) Method 960.09, and according to ASTM (American Society for Testing and Materials) Method E 1153-94, which methods are incorporated herein by reference in their entirety.

TABLE 1

AOAC Method: VigorOx ™ Liquid Sanitizer & Disinfectant, *Xanthomonas axonopodis* pv citrumelo (X100-00139).

| Sample ID | 85 ppm (VigorOx ™) | | | 200 ppm (VigorOx ™) | | |
|---|---|---|---|---|---|---|
| | Numbers Control CFU/ml of test flask | 30 sec. treatment % reduction | 60 sec. treatment % reduction | Numbers Control CFU/ml of test flask | 30 sec. treatment % reduction | 60 sec. treatment % reduction |
| Lot - A | | | | | | |
| Re 1 | 1.94E+08 | <2.5 (>99.99999) | <2.5 (>99.99999) | 1.31E+08 | <2.5 (>99.99999) | <2.5 (>99.99999) |
| Rep 2 | 1.56E+08 | <2.5 (>99.99999) | <2.5 (>99.99999) | 1.20E+08 | <2.5 (>99.99999) | <2.5 (>99.99999) |
| Geom. Mean | 1.74E+08 | | | 1.25E+08 | | |
| Lot - B | | | | | | |
| Re 1 | 1.15E+10 | 6.12E+03 (99.9996) | <2.5 (>99.999999) | 1.53E+08 | <2.5 (>99.99999) | <2.5 (>99.99999) |
| Re 2 | 1.72E+08 | 2.00E+01 (>99.99999) | <2.5 (>99.999999) | 1.46E+08 | <2.5 (>99.99999) | <2.5 (>99.99999) |
| Geom. Mean | 1.41E+09 | | | 1.49E+08 | | |
| Lot - C | | | | | | |
| Re 1 | 1.58E+08 | <2.5 (>99.99999) | <2.5 (>99.99999) | 1.41 E+08 | <2.5 (>99.99999) | <2.5 (>99.99999) |
| Re 2 | 1.60E+08 | <2.5 (>99.99999) | <2.5 (>99.99999) | 1.61 E+08 | <2.5 (>99.99999) | <2.5 (>99.99999) |
| Geom. Mean | 1.59E+08 | | | 1.51 E+08 | | |

TABLE 2

AOAC Method: VigorOx ™ Liquid Sanitizer & Disinfectant, *Xanthomonas campestris* pv citrumelo (X100-00191).

| Sample ID | 85 ppm (VigorOx ™) | | | 200 ppm (VigorOx ™) | | |
|---|---|---|---|---|---|---|
| | Numbers Control CFU/ml of test flask | 30 sec. treatment % reduction | 60 sec. treatment % reduction | Numbers Control CFU/ml of test flask | 30 sec. treatment % reduction | 60 sec. treatment % reduction |
| Lot - A | | | | | | |
| Rep 1 | 1.30E+08 | 4.15E+04 99.966 | 2.00E+02 99.9996 | 1.02E+08 | <2.5 >99.99999 | <2.5 >99.99999 |
| Rep 2 | 1.14E+OS | <2.5 (>99.99999) | <2.5 (>99.99999) | 1.02E+08 | <2.5 (>99.99999) | <2.5 (>99.99999) |
| Geom. Mean | 1.22E+08 | | | 1.02E+08 | | |
| Lot - B | | | | | | |
| Rep 1 | 1.19E+08 | 1.20E+02 (99.9999) | <2.5 (>99.99999) | 1.00E+08 | <2.5 (>99.99999) | <2.5 (>99.99999) |
| Rep 2 | 1.35E+08 | 7.40E+03 (99.994) | <2.5 (>99.99999) | 1.10E+08 | <2.5 (>99.99999) | <2.5 (>99.99999) |
| Geom. Mean | 1.26E+08 | | | 1.05E+08 | | |
| Lot - C | | | | | | |
| Rep 1 | 1.22E+08 | 1.80E+02 (99.9998) | <2.5 (>99.99999) | 1.01 E+08 | <2.5 (>99.99999) | <2.5 (>99.99999) |
| Rep 2 | 1.17E+08 | 1.00E+01 (99.99999) | <2.5 (>99.99999) | 9.30E+07 | <2.5 (>99.99999) | <2.5 (>99.99999) |
| Geom. Mean | 1.19E+08 | | | 9.69E+07 | | |

Note:
% Reduction = (geometric mean of respective number controls)
- (corresponding replication counts)
- (geometric mean of respective number controls × 100.

TABLE 3

AOAC Method: VigorOx ® SP-15 Antimicrobial Agent, *Xanthomonas axonopodis* pv citrumelo (X100-00139).

| Sample ID | 85 ppm (VigorOx ™) | | | 200 ppm (VigorOx ™) | | |
|---|---|---|---|---|---|---|
| | Numbers Control CFU/ml of test flask | 30 sec. treatment % reduction | 60 sec. treatment % reduction | Numbers Control CFU/ml of test flask | 30 sec. treatment % reduction | 60 sec. treatment % reduction |
| Lot - A | | | | | | |
| Re 1 | 1.46E+08 | <2.5 (>99.99999) | <2.5 (>99.99999) | 1.41E+08 | <2.5 (>99.99999) | <2.5 (>99.99999) |
| Rep 2 | 1.52E+08 | 1.00E+01 (99.99999) | <2.5 (>99.99999) | 1.31E+08 | <2.5 (>99.99999) | <2.5 (>99.99999) |
| Geom. Mean | 1.49E+08 | | | 1.36E+08 | | |

TABLE 3-continued

AOAC Method: VigorOx ® SP-15 Antimicrobial Agent, *Xanthomonas axonopodis* pv citrumelo (X100-00139).

| | 85 ppm (VigorOx ™) | | | 200 ppm (VigorOx ™) | | |
|---|---|---|---|---|---|---|
| Sample ID | Numbers Control CFU/ml of test flask | 30 sec. treatment % reduction | 60 sec. treatment % reduction | Numbers Control CFU/ml of test flask | 30 sec. treatment % reduction | 60 sec. treatment % reduction |
| Lot - B | | | | | | |
| Re 1 | 1.39E+08 | 7.00E+01 (99.99995) | <2.5 (>99.999999) | 2.15E+08 | <2.5 (>99.99999) | <2.5 (>99.99999) |
| Re 2 | 1.35E+08 | <2.5 (>99.999999) | <2.5 (>99.999999) | 1.78E+08 | <2.5 (>99.99999) | <2.5 (>99.99999) |
| Geom. Mean | 1.37E+08 | | | 1.97E+08 | | |
| Lot - C | | | | | | |
| Re 1 | 1.47E+08 | 2.80E+02 (99.9998) | <2.5 (>99.99999) | 1.61E+08 | <2.5 (>99.99999) | <2.5 (>99.99999) |
| Rep 2 | 1.72E+08 | 8.00E+01 (99.99995) | <2.5 (>99.99999) | 1.69E+08 | <2.5 (>99.99999) | <2.5 (>99.99999) |
| Geom. Mean | 1.59E+08 | | | 1.65E+08 | | |

TABLE 4

AOAC Method: VigorOx ™ SP-15 Antimicrobial Agent, *Xanthomonas campestris* pv citrumelo (X100-00191).

| | 85 ppm (VigorOx ™) | | | 200 ppm (VigorOx ™) | | |
|---|---|---|---|---|---|---|
| Sample ID | Numbers Control CFU/ml of test flask | 30 sec. treatment % reduction | 60 sec. treatment % reduction | Numbers Control CFU/ml of test flask | 30 sec. treatment % reduction | 60 sec. treatment % reduction |
| Lot - A | | | | | | |
| Rep 1 | 1.70E+08 | <2.5 >99.99999 | <2.5 >99.99999 | 8.80E+07 | <2.5 >99.99999 | <2.5 >99.99999 |
| Rep 2 | 1.16E+08 | 2.80E+02 (99.9998) | <2.5 (>99.99999) | 7.30F+07 | <2.5 (>99.99999) | <2.5 (>99.99999) |
| Geom. Mean | 1.40E+08 | | | 8.01E+07 | | |
| Lot - B | | | | | | |
| Rep 1 | 1.16E+08 | <2.5 (>99.99999) | <2.5 (>99.99999) | 1.08E+08 | <2.5 (>99.99999) | <2.5 (>99.99999) |
| Rep 2 | 1.25E+08 | 9.00E+01 (99.99993) | <2.5 (>99.99999) | 8.40E+07 | <2.5 (>99.99999) | <2.5 (>99.99999) |
| Geom. Mean | 1.20E+08 | | | 9.52E+07 | | |
| Lot - C | | | | | | |
| Rep 1 | 1.39E+08 | 2.00E+01 (99.99999) | <2.5 (>99.99999) | 1.16E+08 | <2.5 (>99.99999) | <2.5 (>99.99999) |
| Rep 2 | 1.52E+08 | 1.21E+03 (99.9992) | <2.5 (>99.99999) | 1.20E+08 | <2.5 (>99.99999) | <2.5 (>99.99999) |
| Geom. Mean | 1.45+08 | | | 1.18E+08 | | |

Note:
% Reduction = (geometric mean of respective number controls)
- (corresponding replication counts)
- (<u>geometric</u> mean of <u>respective</u> number controls × 100.

TABLE 5

ASTM Method: VigorOxTm Liquid Sanitizer & Disinfectant (85 ppm), *Xanthomonas axonopodis* pv citrumelo (X100-00139).

| | Duplicate #1 | | Duplicate #2 | |
|---|---|---|---|---|
| Sample ID | CONTROL | TREATED | CONTROL | TREATED |
| Lot - A CFU/ test square | | | | |
| Rep. 1 | 1.25E+06 | <12.5 | 1.18E+06 | <12.5 |
| Rep. 2 | 2.75E+05 | <12.5 | 2.75E+05 | <12.5 |
| Rep. 3 | 1.18E+06 | <12.5 | 1.08E+06 | <12.5 |
| Rep. 4 | N/A | <12.5 | N/A | <12.5 |
| Rep. 5 | N/A | <12.5 | N/A | <12.5 |
| Geom. Mean reduction | 7.40E+05 >99.998 | <12.5 | 7.05E+05 >99.998 | <12.5 |
| Lot - B | | | | |
| Rep. 1 | 1.90E+06 | <12.5 | 1.35E+06 | <12.5 |
| Rep. 2 | 1.70E+06 | <12.5 | 1.20E+06 | <12.5 |

TABLE 5-continued

ASTM Method: VigorOxTm Liquid Sanitizer &
Disinfectant (85 ppm), *Xanthomonas axonopodis* pv citrumelo (X100-00139).

| Sample ID | Duplicate #1 | | Duplicate #2 | |
|---|---|---|---|---|
| | CONTROL | TREATED | CONTROL | TREATED |
| Rep. 3 | 8.00E+05 | <12.5 | 7.75E+05 | <12.5 |
| Rep. 4 | N/A | <12.5 | N/A | <12.5 |
| Rep. 5 | N/A | <12.5 | N/A | <12.5 |
| Geom. Mean | 1.37E+06 | <12.5 | 1.08E+06 | <12.5 |
| reduction | >99.999 | | >99.998 | |
| Lot - C | | | | |
| Rep. 1 | 3.15E+06 | <12.5 | 2.20E+06 | <12.5 |
| Rep. 2 | 9.20E+06 | <12.5 | 8.80E+06 | <12.5 |
| Rep. 3 | 3.40E+06 | <12.5 | 1.60E+06 | <12.5 |
| Rep. 4 | N/A | <12.5 | N/A | <12.5 |
| Rep. 5 | N/A | <12.5 | N/A | <12.5 |
| Geom. Mean | 4.62E+06 | <12.5 | 3.14E+06 | <12.5 |
| reduction | >99.999 | | >99.999 | |

Note:
% Reduction = (geometric mean of respective number controls)

TABLE 6

ASTM Method: VigorOxTm Liquid Sanitizer &
Disinfectant (140 ppm), *Xanthomonas axonopodis* pv citrumelo (X100-00139).

| Sample ID | Duplicate #1 | | Duplicate #2 | |
|---|---|---|---|---|
| | CONTROL | TREATED | CONTROL | TREATED |
| Lot - A CFU/ test square | | | | |
| Rep. 1 | 3.25E+05 | <12.5 | 3.00E+05 | <12.5 |
| Rep. 2 | 5.00E+05 | <12.5 | 3.75E+05 | <12.5 |
| Rep. 3 | 5.25E+05 | <12.5 | 4.00E+05 | <12.5 |
| Rep. 4 | N/A | <12.5 | N/A | <12.5 |
| Rep. 5 | N/A | <12.5 | N/A | <12.5 |
| Geom. Mean | 4.40E+05 | <12.5 | 3.56E+05 | <12.5 |
| reduction | >99.997 | | >99.996 | |
| Lot - B | | | | |
| Rep. 1 | 1.55E+06 | <12.5 | 1.63E+06 | <12.5 |
| Rep. 2 | 1.24E+07 | <12.5 | 6.60E+06 | <12.5 |
| Rep. 3 | 6.23E+06 | <12.5 | 7.60E+06 | <12.5 |
| Rep. 4 | N/A | <12.5 | N/A | <12.5 |
| Rep. 5 | N/A | <12.5 | N/A | <12.5 |
| Geom. Mean | 4.93E+06 | <12.5 | 4.34E+06 | <12.5 |
| reduction | >99.999 | | >99.999 | |
| Lot - C | | | | |
| Rep. 1 | 1.10E+06 | <12.5 | 3.50E+06 | <12.5 |
| Rep. 2 | 1.18E+06 | <12.5 | 1.63E+06 | <12.5 |
| Rep. 3 | 1.15E+06 | <12.5 | 9.00E+05 | <12.5 |
| Rep. 4 | N/A | <12.5 | N/A | <12.5 |
| Rep. 5 | N/A | <12.5 | N/A | <12.5 |
| Geom. Mean | 1.14E+06 | <12.5 | 1.73E+06 | <12.5 |
| reduction | >99.998 | | >99.999 | |

- (geometric mean of corresponding replication counts)
(geometric mean of respective number controls) × 101

TABLE 7

ASTM Method: VigorO)(m Liquid Sanitizer &
Disinfectant (200 ppm), *Xanthomonas axonopodis* pv citrumelo (X100-00139).

| Sample ID | Duplicate #1 | | Duplicate #2 | |
|---|---|---|---|---|
| | CONTROL | TREATED | CONTROL | TREATED |
| Lot - A CFU/ test square | | | | |
| Rep. 1 | 5.68E+06 | <12.5 | 4.35E+06 | <12.5 |
| Rep. 2 | 2.73E+06 | <12.5 | 2.75E+06 | <12.5 |
| Rep. 3 | 1.98E+06 | <12.5 | 1.75E+06 | <12.5 |
| Rep. 4 | N/A | <12.5 | N/A | <12.5 |
| Rep. 5 | N/A | <12.5 | N/A | <12.5 |
| Geom. Mean | 3.13E+06 | <12.5 | 2.76E+06 | <12.5 |
| reduction | >99.999 | | >99.999 | |
| Lot - B | | | | |
| Rep. 1 | 1.06E+06 | <12.5 | 1.80E+06 | <12.5 |
| Rep. 2 | 2.10E+06 | <12.5 | 2.53E+06 | <12.5 |
| Rep. 3 | 1.23E+06 | <12.5 | 1.05E+06 | <12.5 |
| Rep. 4 | N/A | <12.5 | N/A | <12.5 |
| Rep. 5 | N/A | <12.5 | N/A | <12.5 |
| Geom. Mean | 1.60E+06 | <12.5 | 1.68E+06 | <12.5 |
| reduction | >99.999 | | >99.999 | |
| Lot - C | | | | |
| Rep. 1 | 1.70E+06 | <12.5 | 1.48E+06 | <12.5 |
| Rep. 2 | 2.05E+06 | <12.5 | 2.28E+06 | <12.5 |
| Rep. 3 | 1.45E+06 | <12.5 | 1.85E+06 | <12.5 |
| Rep. 4 | N/A | <12.5 | N/A | <12.5 |
| Rep. 5 | N/A | <12.5 | N/A | <12.5 |
| Geom. Mean | 1.72E+06 | <12.5 | 1.84E+06 | <12.5 |
| reduction | >99.999 | | >99.999 | |

*Indicates numbers used to calculate % reduction.

TABLE 8

ASTM Method: VigorOxTm Liquid Sanitizer & Disinfectant (85 ppm),
*Xanthomonas campestris* pv citrumelo (X100-00191).

| Sample ID | Duplicate #1 | | Duplicate #2 | |
|---|---|---|---|---|
| | CONTROL | TREATED | CONTROL | TREATED |
| Lot - A CFU/ test square | | | | |
| Rep. 1 | 1.13E+05* | <12.5 | 1.75E+05 | <12.5 |
| Rep. 2 | 2.50E+04* | <12.5 | 2.50E+04 | <12.5 |
| Rep. 3 | <1.25E+04 | <12.5 | 2.50E+04 | <12.5 |
| Rep. 4 | N/A | <12.5 | N/A | <12.5 |
| Rep. 5 | N/A | <12.5 | N/A | <12.5 |
| Geom. Mean | 5.32E+04* | <12.5 | 4.78E+04 | <12.5 |
| reduction | >99.98* | | >99.97 | |
| Lot - B | | | | |
| Rep. 1 | 4.00E+05 | <12.5 | 3.25E+05 | <12.5 |
| Rep. 2 | 3.73E+06 | <12.5 | 3.15E+06 | <12.5 |
| Rep. 3 | 1.69E+06 | <12.5 | 1.70E+06 | <12.5 |
| Rep. 4 | N/A | <12.5 | N/A | <12.5 |
| Rep. 5 | N/A | <12.5 | N/A | <12.5 |
| Geom. Mean | 1.36E+06 | <12.5 | 1.20E+06 | <12.5 |
| reduction | >99.999 | | >99.998 | |
| Lot - C | | | | |
| Rep. 1 | 5.00E+04 | <12.5 | 6.25E+04 | <12.5 |
| Rep. 2 | 2.13E+07 | <12.5 | 2.28E+07 | <12.5 |
| Rep. 3 | 1.39E+06 | <12.5 | 1.39E+06 | <12.5 |
| Rep. 4 | N/A | <12.5 | N/A | <12.5 |
| Rep. 5 | N/A | <12.5 | N/A | <12.5 |
| Geom. Mean | 1.14E+06 | <12.5 | 1.26E+06 | <12.5 |
| reduction | >99.998 | | –>99.999 | |

TABLE 8-continued

ASTM Method: VigorOxTm Liquid Sanitizer & Disinfectant (85 ppm), Xanthomonas campestris pv citrumelo (X100-00191).

|  | Duplicate #1 | | Duplicate #2 | |
|---|---|---|---|---|
| Sample ID | CONTROL | TREATED | CONTROL | TREATED |

Note:
% Reduction = (geometric mean of respective number controls)
- (geometric mean of corresponding replication counts)
(geometric mean of respective number controls) × 100

TABLE 9

ASTM Method: VigorOxTM Liquid Sanitizer & Disinfectant (140 ppm), Xanthomonas campestris pv citrumelo (X100-00191).

|  | Duplicate #1 | | Duplicate #2 | |
|---|---|---|---|---|
| Sample ID | CONTROL | TREATED | CONTROL | TREATED |
| Lot - A CFU/ test square | | | | |
| Rep. 1 | 1.14E+07 | <12.5 | 1.33E+07 | <12.5 |
| Rep. 2 | 7.08E+06 | <12.5 | 1.74E+06 | <12.5 |
| Rep. 3 | 1.25E+04 | <12.5 | 1.25E+04 | <12.5 |
| Rep. 4 | N/A | <12.5 | N/A | <12.5 |
| Rep. 5 | N/A | <12.5 | N/A | <12.5 |
| Geom. Mean | 1.00E+06 | <12.5 | 1.07E+06 | <12.5 |
| reduction | >99.998 | | >99.998 | |
| Lot - B | | | | |
| Rep. 1 | 5.38E+05 | <12.5 | 5.88E+05 | <12.5 |
| Rep. 2 | 6.25E+04 | <12.5 | 1.25E+04 | <12.5 |
| Rep. 3 | 2.50E+04 | <12.5 | 2.50E+04 | <12.5 |
| Rep. 4 | N/A | <12.5 | N/A | <12.5 |
| Rep. 5 | N/A | <12.5 | N/A | <12.5 |
| Geom. Mean | 9.44E+04 | <12.5 | 5.69E+04 | <12.5 |
| reduction | >99.98 | | >99.97 | |
| Lot - C | | | | |
| Rep. 1 | 2.50E+04* | <12.5 | <1.25E+04 | <12.5 |
| Rep. 2 | <1.25E+04 | <12.5 | <1.25E+04 | <12.5 |
| Rep. 3 | 1.25E+04* | <12.5 | 3.75E+04* | <12.5 |
| Rep. 4 | N/A | <12.5 | N/A | <12.5 |
| Rep. 5 | N/A | <12.5 | N/A | <12.5 |
| Geom. Mean | 1.77E+04* | <12.5 | 3.75E+04* | <12.5 |
| reduction | >99.9* | | >99.96* | |

*Indicates numbers used to calculate % reduction.
Note:
% Reduction = (geometrlc mean of respective number controls)

TABLE 10

ASTM Method: VigorOxTm Liquid Sanitizer & Disinfectant (200 ppm), Xanthomonas campestris pv citrumelo (X100-00191).

|  | Duplicate #1 | | Duplicate #2 | |
|---|---|---|---|---|
| Sample ID | CONTROL | TREATED | CONTROL | TREATED |
| Lot - A CFU/ test square | | | | |
| Rep. 1 | 1.25E+04* | <12.5 | 5.00E+04 | <12.5 |
| Rep. 2 | 1.13E+05* | <12.5 | 7.50E+04 | <12.5 |
| Rep. 3 | <1.25E+04 | <12.5 | 1.25E+04 | <12.5 |
| Rep. 4 | N/A | <12.5 | N/A | <12.5 |
| Rep. 5 | N/A | <12.5 | N/A | <12.5 |
| Geom. Mean | 3.76E+04* | <12.5 | 3.61E+04 | <12.5 |
| reduction | >99.96* | | >99.96 | |

TABLE 10-continued

ASTM Method: VigorOxTm Liquid Sanitizer & Disinfectant (200 ppm), Xanthomonas campestris pv citrumelo (X100-00191).

|  | Duplicate #1 | | Duplicate #2 | |
|---|---|---|---|---|
| Sample ID | CONTROL | TREATED | CONTROL | TREATED |
| Lot - B | | | | |
| Rep. 1 | 5.00E+04* | <12.5 | LOGE+05* | <12.5 |
| Rep. 2 | <1.25E+04 | <12.5 | 1.25E+04* | <12.5 |
| Rep. 3 | 1.25E+04* | <12.5 | <1.25E+04 | <12.5 |
| Rep. 4 | N/A | <12.5 | N/A | <12.5 |
| Rep. 5 | N/A | <12.5 | N/A | <12.5 |
| Geom. Mean | 2.50E+04* | <12.5 | 3.54E+04* | <12.5 |
| reduction | >99.95* | | >99.95* | |
| Lot - C | | | | |
| Rep. 1 | 6.25E+04* | <12.5 | 2.50E+04 | <12.5 |
| Rep. 2 | 6.25E+04* | <12.5 | 2.50E+04 | <12.5 |
| Rep. 3 | <1.25E+04 | <12.5 | 2.50E+04 | <12.5 |
| Rep. 4 | N/A | <12.5 | N/A | <12.5 |
| Rep. 5 | N/A | <12.5 | N/A | <12.5 |
| Geom. Mean | 6.25E+04* | <12.5 | 2.50E+04 | <12.5 |
| reduction | >99.98* | | >99.94 | |

- (geometric mean of corresponding replication counts)
(geometric mean of respective number controls) × 100.

EXAMPLE 2

Materials and Methods

Four strains of *X. axonopodis* pv. *citrumelo* were obtained from the Florida Department of Citrus and propagated in Nutrient Broth (Difco) at 22° C. with agitation for 48 to 72 hours. Cells were pelleted at 5,000 rpm/16 minutes, washed with Butterfield's Phosphate (pH 7.2) and resuspended in approximately 10% of the initial culture volume with Butterfield's Phosphate in order to concentrate the cells 10×. This final concentrate was used as the inoculum for the dose-response study. FMC VigorOx Liquid Sanitizer and Disinfectant (5% peracetic acid) and VigorOx SP-15 Antimicrobial Agent (15% peracetic acid) were diluted to final peracetic acid concentrations of 0 ppm (control), 5 ppm, 10 ppm, 20 ppm, 30 ppm, 40 ppm, 50 ppm, 60 ppm, 70 ppm, and 80 ppm with distilled water. Each variable was dispensed in 9.9 ml aliquots in sterile test tubes.

A 0.1 ml aliquot of the inoculum was added to each peracetic acid variable, shaken, and allowed to remain exposed to the solution for 1 minute. After 1 minute, 1 ml of the inoculated solution was added to 9 ml of Letheen broth (Difco)+0.5% Sodium Thiosulfate (J. T. Baker) to stop the reaction. The solutions were plated on Nutrient Agar (Difco) using a spread plate method and incubated at 22° C. for 72 hours before enumeration. Each concentration variable trial of each product was replicated in triplicate, and each variable was plated in duplicate.

Results

Data summaries of trials performed on each product are expressed in the following tables. The data expressed for each variable is the mean of three replicates. The initial inoculum was determined to contain $2.9 \times 10^{11}$ cfu/ml *X. axonopodis*, and the initial level of *X. axonopodis* exposed to each concentration of peracetic acid was determined to be $2.9 \times 10^9$ cfu/ml.

TABLE 11

Dose-response of X. axonopodis to VigorOx Liquid Sanitizer and Disinfectant (5% peracetic acid)

| Concentration (ppm) | cfu/ml after 1 minute exposure | Calculated reduction of X. axonopodis ($\log_{10}$ cfu/ml) |
|---|---|---|
| 0 (control) | >>6.0 × 10$^{8*}$ | 0 |
| 5 | >>6.0 × 10$^{8*}$ | 0 |
| 10 | >>6.0 × 10$^{8*}$ | 0 |
| 20 | 2.6 × 10$^7$ | 2.05 |
| 30 | <1.0 × 10$^1$ | >8.46 |
| 40 | <1.0 × 10$^1$ | >8.46 |
| 50 | <1.0 × 10$^1$ | >8.46 |
| 60 | <1.0 × 10$^1$ | >8.46 |
| 70 | <1.0 × 10$^1$ | >8.46 |
| 80 | <1.0 × 10$^1$ | >8.46 |

*Estimated count per FDA's Bacteriological Analytical Manual, 8$^{th}$ Edition, Chapter 3, which is incorporated by reference herein in its entirety.

TABLE 12

Dose-response of X. axonopodis to VigorOx SP-15 Antimicrobial Agent (5% peracetic acid)

| Concentration (ppm) | cfu/ml after 1 minute exposure | Calculated reduction of X. axonopodis ($\log_{10}$ cfu/ml) |
|---|---|---|
| 0 (control) | >>6.0 × 10$^{8*}$ | 0 |
| 5 | >>6.0 × 10$^{8*}$ | 0 |
| 10 | >>6.0 × 10$^{8*}$ | 0 |
| 20 | 1.0 × 10$^7$ | 2.46 |
| 30 | <1.0 × 10$^1$ | >8.46 |
| 40 | <1.0 × 10$^1$ | >8.46 |
| 50 | <1.0 × 10$^1$ | >8.46 |
| 60 | <1.0 × 10$^1$ | >8.46 |
| 70 | <1.0 × 10$^1$ | >8.46 |
| 80 | <1.0 × 10$^1$ | >8.46 |

*Estimated count per FDA's Bacteriological Analytical Manual, 8$^{th}$ Edition, Chapter 3.

Conclusion

A concentration of greater than 10 parts per million but less than 20 parts per million of peroxyacetic acid produces a significant reduction (>1 $\log_{10}$ cfu/ml) of the bacterial citrus pathogen organism X. axonopodis, and 30 parts per million peroxyacetic acid, and above, produce a reduction of >99.9%.

In the specification there have been disclosed a typical preferred embodiment of the invention, and although specific terms are employed, the terms are used in a descriptive sense only and not for purposes of limitation. The invention has been described in considerable detail, however, it will be apparent that various modifications and changes can be made within the spirit and scope of the invention as described in the foregoing specification and as defined in the appended claims.

That which is claimed:

1. A process of disinfecting citrus fruit, comprising contacting the fruit with a composition effective against a pathovar of *Xanthomonas axonopodis* pathogenic for citrus, wherein the composition comprises an aqueous solution of a carboxylic acid, hydrogen peroxide, and a percarboxylic acid product thereof, and the percarboxylic acid is present at a concentration of less than 200 parts per million.

2. The process of claim 1, wherein said contacting comprises a time sufficient for reducing the pathovar by at least 99.9%.

3. The process of claim 1, wherein said contacting is sufficient to reduce the pathovar by at least 99.9% within approximately one minute.

4. The process of claim 1, wherein the composition further comprises up to approximately 1% by weight sulfuric acid.

5. The process of claim 1, further including drying after contacting.

6. A process of disinfecting citrus fruit, comprising contacting the fruit with a composition effective against a pathovar of *Xanthomonas axonopodis* pathogenic for citrus, wherein the composition comprises an aqueous solution of acetic acid, hydrogen peroxide, and peroxyacetic acid, and the peroxyacetic acid is present at a concentration of less than 200 parts per million in equilibrium with said hydrogen peroxide and acetic acid.

7. The process of claim 6, wherein said contacting comprises a time sufficient for reducing the pathovar by at least 99.9%.

8. The process of claim 6, wherein contacting is sufficient to reduce the pathovar by at least 99.9% within approximately one minute.

9. The process of claim 6, wherein the composition further comprises up to approximately 1% by weight sulfuric acid.

10. The process of claim 6, further including drying after contacting.

11. A process of disinfecting equipment used with citrus fruit, comprising contacting the equipment with a composition effective against a pathovar of *Xanthomonas axonopodis* pathogenic for citrus, wherein the composition comprises an aqueous solution of a carboxylic acid, hydrogen peroxide, and a percarboxylic acid product thereof, and the percarboxylic acid is present at a concentration of less than 200 parts per million.

12. The process of claim 11, wherein said contacting comprises a time sufficient for reducing the pathovar by at least 99.9%.

13. The process of claim 11, wherein said contacting is sufficient to reduce the pathovar by at least 99.9% within approximately five minutes.

14. The process of claim 11, wherein the composition further comprises up to approximately 1% by weight sulfuric acid.

15. The process of claim 11, further including drying after contacting.

16. A process of disinfecting equipment used with citrus fruit, comprising contacting the equipment with a composition effective against a pathovar of *Xanthomonas axonopodis* pathogenic for citrus, wherein the composition comprises an aqueous solution of acetic acid, hydrogen peroxide, and peroxyacetic acid, and the peroxyacetic acid is present at a concentration of less than 200 parts per million in equilibrium with said hydrogen peroxide and acetic acid.

17. The process of claim 16, wherein said contacting comprises a time sufficient for reducing the pathovar by at least 99.9%.

18. The process of claim 16, wherein said contacting is sufficient to reduce the pathovar by at least 99.9% within approximately five minutes.

19. The process of claim 16, wherein the composition further comprises up to approximately 1% by weight sulfuric acid.

20. The process of claim 16, further including drying after contacting.

* * * * *

UNITED STATES PATENT AND TRADEMARK OFFICE
CERTIFICATE OF CORRECTION

PATENT NO.    : 6,506,417 B1
DATED         : January 14, 2003
INVENTOR(S)   : John M. Siddle It is certified that error appears in the above-identified patent and that said Letters Patent is hereby corrected as shown below:

Title page,
Item [56], OTHER PUBLICATIONS,
Delete "D. COATES," reference in its entirety and insert: -- D. COATES, *Sporicidal activity of sodium dichloroisocyanurate, peroxygen and glutaraldehyde disinfectants against Bacillus subtilis*, Journal of Hospital Infection, 1996, 32, (pp. 283-294) --
Delete "Anouar Alasri, Michele Valverde, Christine Roques and Georges Michel and Corinne Cabassud and Philippe Aptel," reference in its entirety and insert:
-- Anouar Alasri, Michele Valverde, Christine Roques and Georges Michel and Corinne Cabassud and Philippe Aptel, *Sporocidal properties of peracetic acid and hydrogen peroxide, alone and in combination, in comparison with chlorine and formaldehyde for ultrafiltration membrane disinfection*, Can. J. Microbiol., Vol. 39, 1993 Toulouse, France, (pp 52-60) --

Column 2,
Line 4, delete "plants" insert -- plant --

Column 3,
Line 4, delete "percaboxylic" insert -- percarboxylic --
Line 10, delete "$CH_3COOH + H_2O \leftrightarrows CH_3COOOH + H_2O$" insert
-- $CH_3COOH + H_2O_2 \leftrightarrows CH_3COOOH + H_2O$ --
Line 65, delete "contacting.optionally" insert -- contacting optionally --

Column 5,
Table 2, 4th Column, delete "99.9996" insert -- 99.9998 --
Table 3, Heading, delete "VigorOx®" insert -- VigorOx$^{TM}$ --

Column 7,
Table 3-continued, Heading, delete "VigorOx®" insert -- VigorOx$^{TM}$ --
Table 4, 2nd Column, delete "1.45+08" insert -- 1.45E+08 --
Line 52, Table 5, Heading, delete "VigorOxTm" insert -- VigorOx$^{TM}$ --

Column 8,
Table 4, 5th Column, delete "7.30F+07" insert -- 7.30E+07 --
Line 52, Table 5-continued, Heading, delete "VigorOxTm" insert -- VigorOx$^{TM}$ --

Column 9,
Line 4, Table 5-continued, Heading, delete "VigorOxTm" insert -- VigorOx$^{TM}$ --
Line 36, Table 6, Heading, delete "VigorOxTm" insert -- VigorOx$^{TM}$ --

UNITED STATES PATENT AND TRADEMARK OFFICE
CERTIFICATE OF CORRECTION

PATENT NO. : 6,506,417 B1
DATED : January 14, 2003
INVENTOR(S) : John M. Siddle

It is certified that error appears in the above-identified patent and that said Letters Patent is hereby corrected as shown below:

<u>Column 10,</u>
Line 4, Table 7, Heading, delete "VigorO)(m" insert -- VigorOx$^{TM}$ --
Line 19, Table 7, 2$^{nd}$ Column, delete "1.06E+06" insert -- 1.60E+06 --
Line 38, Table 8, Heading, delete "VigorOxTm" insert -- VigorOx$^{TM}$ --

<u>Column 11,</u>
Line 4, Table 8-continued, Heading, delete "VigorOxTm" insert -- VigorOx$^{TM}$ --
Line 17, Table 9, Heading, delete "VigorOxTM" insert -- VigorOx$^{TM}$ --
Line 28, Table 9, 4$^{th}$ Column, delete "1.74E+06" insert -- 7.41E+06 --
Line 49, Table 9, delete "geometrlc" insert -- geometric --
Line 53, Table 10, Heading, delete "VigorOxTm" insert -- VigorOx$^{TM}$ --

<u>Column 12,</u>
Line 4, Table 10-continued, Heading, delete "VigorOxTm" insert -- VigorOx$^{TM}$ --

<u>Column 14,</u>
Line 24, delete "wherein contacting" insert -- wherein said contacting --

Signed and Sealed this

Tenth Day of June, 2003

JAMES E. ROGAN
*Director of the United States Patent and Trademark Office*

(12) EX PARTE REEXAMINATION CERTIFICATE (5395th)
United States Patent
Siddle

(10) Number: US 6,506,417 C1
(45) Certificate Issued: Jun. 6, 2006

(54) COMPOSITION AND PROCESS FOR REDUCING BACTERIAL CITRUS CANKER ORGANISMS

(75) Inventor: John M. Siddle, Lakeland, FL (US)

(73) Assignee: FMC Technologies, Inc., Chicago, IL (US)

Reexamination Request:
No. 90/006,777, Sep. 19, 2003

Reexamination Certificate for:
Patent No.: 6,506,417
Issued: Jan. 14, 2003
Appl. No.: 09/894,570
Filed: Jun. 28, 2001

Certificate of Correction issued Jun. 10, 2003.

(51) Int. Cl.
*A01H 37/00* (2006.01)
*A01H 37/16* (2006.01)
*A01H 59/00* (2006.01)
*A61L 21/18* (2006.01)
*A23L 3/34* (2006.01)

(52) U.S. Cl. .................. 424/616; 514/557; 514/558; 514/559; 514/560; 514/568; 514/572; 514/574; 514/714; 422/28; 422/29; 426/333; 426/335; 426/532

(58) Field of Classification Search .................. None
See application file for complete search history.

(56) References Cited

U.S. PATENT DOCUMENTS

| | | |
|---|---|---|
| 4,051,058 A | 9/1977 | Bowing et al. |
| 4,587,264 A | 5/1986 | Jourdan-Laforte et al. |
| 5,508,046 A | 4/1996 | Cosentino et al. |
| 5,674,538 A | 10/1997 | Lokkesmoe et al. |
| 6,302,968 B1 | 10/2001 | Baum et al. |

OTHER PUBLICATIONS

Dairy Research & Info. Center, An Introduction to Bacteria; http://drinc.ucdavis.edu/html/dairy/index.html.
DialysisEthics.org; Peracetic Acid Studies, Hazardous Substance Data Bank, http://www.dialysisethics.org/fyi/canada%20oha.htm.
Florida Department of Agriculture and Consumer Services; http://www.doacs.state.fl.us/canker/pubs/cc–science–pubs.htm; Science Questions & Answers.
Howard Hughs Medical Institute; Peracetic Acid (And Related Percarboxylic Acids); http://www.hhmi.org/research/labsafe/lcss/lcss68.html.
Kim et al.; Monitoring and Characterization of Bacterial Contamination in a High–Purity Water System Used for Semiconductor Manufacturing; The Journal of Microbiology (2000).
Shciff, PhD; Choosing the Proper Sanitizer of Disinfectant; http://www.schiff–consulting.com/choosing.html.
Sterilization vs. Disinfection; A Reference Guide to the Difference Between; http://www.steamatic–cr.com/bioclean/PRINCIPLES.html.
Tech Talk; Baxter Instrument Services; vol. 2002, Issue 44; http://www.baxter.com/doctors/renal_therapies/techpubs/tt44.pdf.
Eldon Brown and T.S. Schubert; Use of Xanthomonas Campestris pv. Vesicatoria to Evaluate Surface Disinfectants for Canker Quarantine Treatment of Citrus Fruit; Plant Disease, vol. 71 #4.

*Primary Examiner*—S. Mark Clardy

(57) ABSTRACT

A disinfectant composition is disclosed effective against a pathovar of Xanthomonas axonopodis pathogenic for citrus, comprising an aqueous solution of a carboxylic acid, hydrogen peroxide, and a percarboxylic acid product thereof. In a preferred composition the percarboxylic acid comprises peroxyacetic acid in an equilibrium aqueous solution with hydrogen peroxide, and acetic acid. The composition is used in a process to disinfect citrus fruit and equipment used therewith by contacting with a sufficient concentration of the composition for a sufficient time for reducing the organisms by at least 99.9%.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–20 is confirmed.

* * * * *